(12) United States Patent
Sidebotham et al.

(10) Patent No.: US 8,696,715 B2
(45) Date of Patent: Apr. 15, 2014

(54) LOW PROFILE MEDICAL LOCKING PLATE AND BONE SCREW DESIGN FOR BONE FRACTURES

(76) Inventors: Chris Sidebotham, Mendham, NJ (US); Leon Roitburg, East Hanover, NJ (US)

( * ) Notice: Subject to any disclaimer, the term of this patent is extended or adjusted under 35 U.S.C. 154(b) by 671 days.

(21) Appl. No.: 12/817,795

(22) Filed: Jun. 17, 2010

(65) Prior Publication Data
US 2011/0313421 A1 Dec. 22, 2011

(51) Int. Cl.
A61B 17/80 (2006.01)
(52) U.S. Cl.
USPC .................... 606/291; 606/290; 606/294
(58) Field of Classification Search
USPC .............. 411/247–252, 353, 999; 606/70–71, 606/280–281, 286–287, 289–294
See application file for complete search history.

(56) References Cited

U.S. PATENT DOCUMENTS

| | | | |
|---|---|---|---|
| 1,161,647 A * | 11/1915 | Finkbeiner | 411/252 |
| 4,493,317 A | 1/1985 | Klaue | |
| 5,578,034 A * | 11/1996 | Estes | 606/281 |
| 5,601,553 A | 2/1997 | Trebing et al. | |
| 5,709,686 A | 1/1998 | Talos et al. | |
| 5,741,258 A * | 4/1998 | Klaue et al. | 606/70 |
| 5,876,402 A | 3/1999 | Errico et al. | |
| 5,951,557 A | 9/1999 | Luter | |
| 6,261,291 B1 * | 7/2001 | Talaber et al. | 606/281 |
| 6,454,770 B1 * | 9/2002 | Klaue | 606/281 |
| 6,533,786 B1 | 3/2003 | Needham et al. | |
| 6,602,255 B1 | 8/2003 | Campbell et al. | |
| 6,623,486 B1 | 9/2003 | Weaver et al. | |
| 6,656,181 B2 * | 12/2003 | Dixon et al. | 606/291 |
| 6,755,833 B1 | 6/2004 | Paul et al. | |
| 7,070,599 B2 | 7/2006 | Paul | |
| 7,128,744 B2 | 10/2006 | Weaver et al. | |
| 7,137,987 B2 * | 11/2006 | Patterson et al. | 606/291 |
| 7,255,699 B2 | 8/2007 | Paul | |
| 7,341,589 B2 | 3/2008 | Weaver et al. | |
| 7,909,859 B2 * | 3/2011 | Mosca et al. | 606/289 |
| 7,955,362 B2 * | 6/2011 | Erickson et al. | 606/289 |
| 8,287,542 B2 * | 10/2012 | Wolter | 606/71 |
| 2004/0181227 A1 | 9/2004 | Khalili | |
| 2005/0192578 A1 * | 9/2005 | Horst | 606/69 |
| 2005/0261688 A1 | 11/2005 | Grady, Jr. et al. | |

(Continued)

FOREIGN PATENT DOCUMENTS

| GB | 2438502 | 11/2007 |
|---|---|---|
| WO | WO2006/029274 | 3/2006 |

(Continued)

Primary Examiner — Nicholas Woodall
Assistant Examiner — Larry E Waggle, Jr.
(74) Attorney, Agent, or Firm — Klarquist Sparkman, LLP

(57) ABSTRACT

Disclosed embodiments of a low profile bone plate can allow for a locking relationship between the bone plate and one or more bone screws, without requiring specialized bone screws. According to the disclosure, a locking element and/or a flange can be provided in one or more through-holes in the bone plate to engage with the threads of the bone screw, to lock the screw in place. Locking elements, such as a straight wire or spring coil positioned near the bone-contacting surface of the bone plate can have a cross sectional diameter less than the pitch of the bone screw threads, so as not to interfere with insertion and tightening of the bone screw. Thus, standard bone screws without threaded heads or tapered shafts can be locked with a bone plate having a minimal thickness, which can advantageously improve chances of wound healing.

31 Claims, 8 Drawing Sheets

(56) References Cited

U.S. PATENT DOCUMENTS

| | | |
|---|---|---|
| 2005/0283152 A1 | 12/2005 | Lindemann et al. |
| 2007/0055251 A1* | 3/2007 | Huebner et al. ............... 606/69 |
| 2007/0162019 A1 | 7/2007 | Burns et al. |
| 2008/0243192 A1 | 10/2008 | Jacene et al. |
| 2009/0054930 A1* | 2/2009 | Aflatoon ...................... 606/246 |
| 2011/0184415 A1* | 7/2011 | Anderson et al. .............. 606/70 |
| 2011/0230969 A1* | 9/2011 | Biedermann et al. ...... 623/17.16 |

FOREIGN PATENT DOCUMENTS

| | | |
|---|---|---|
| WO | WO2007/076050 | 7/2007 |
| WO | WO2008/118599 | 10/2008 |
| WO | WO2008077493 | * 11/2008 |

* cited by examiner

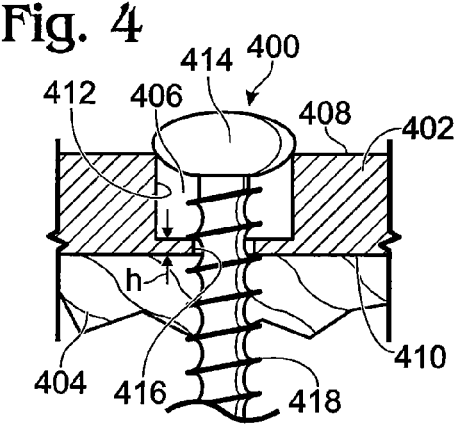
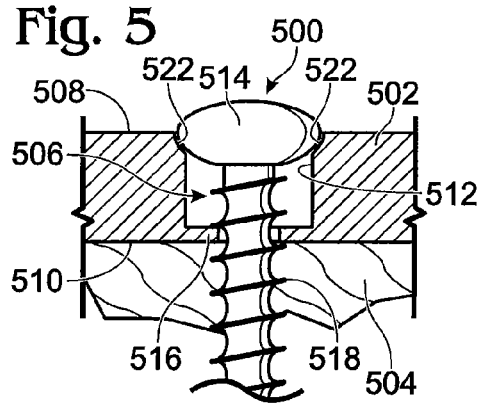
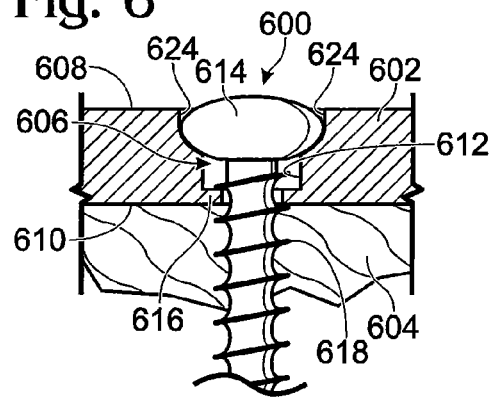
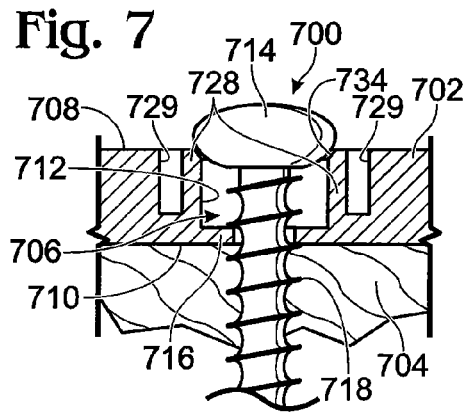
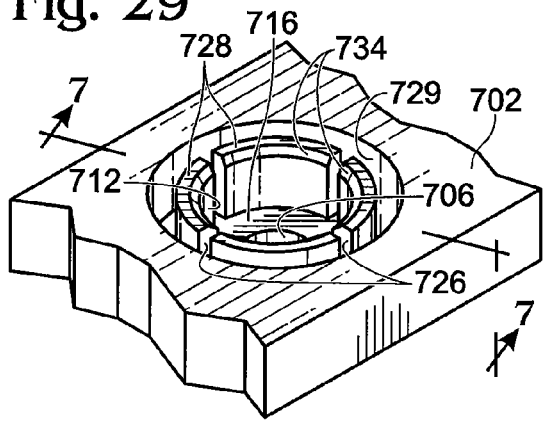

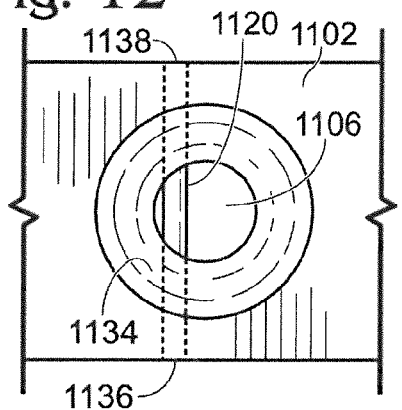
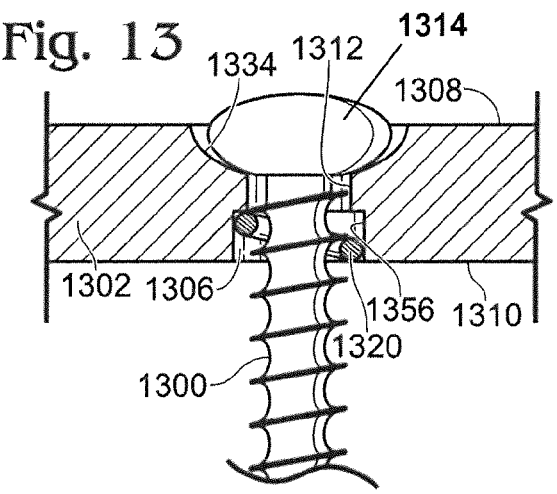
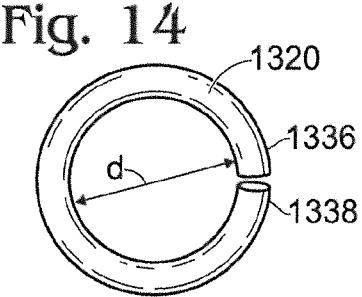
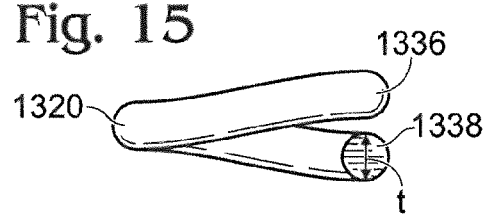
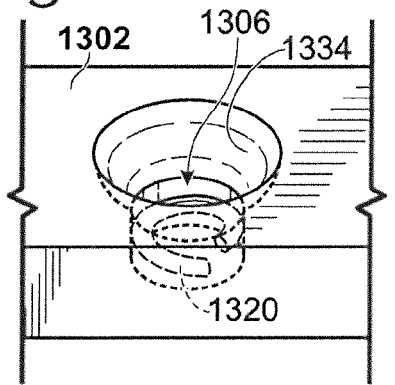
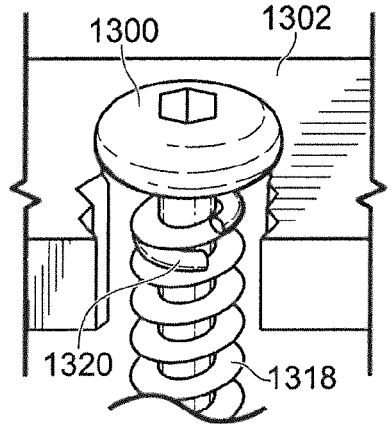

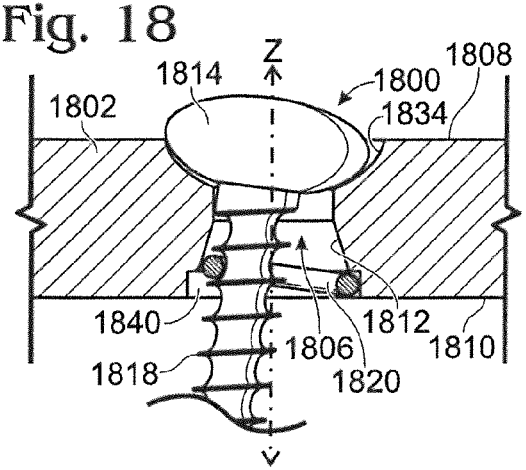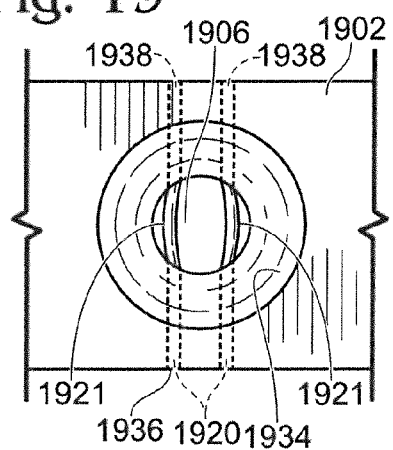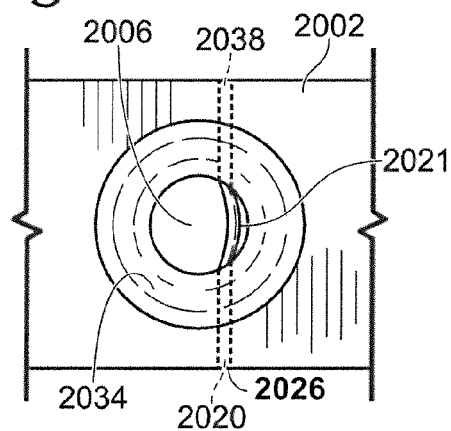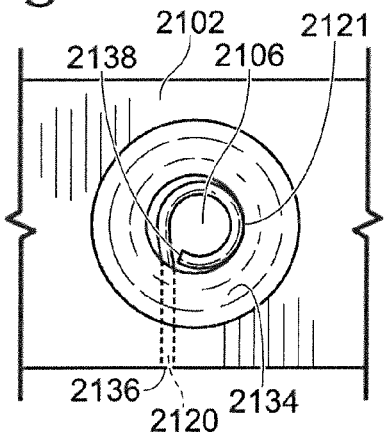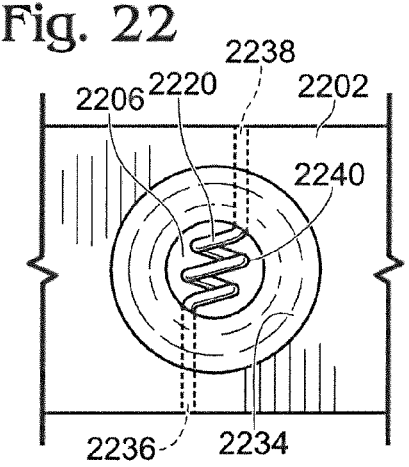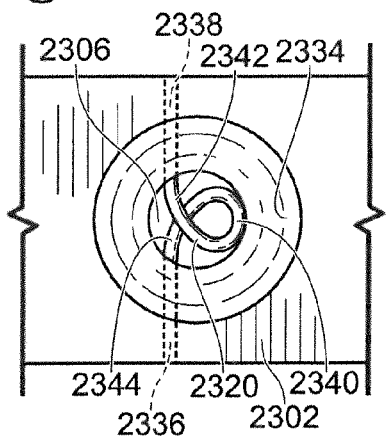

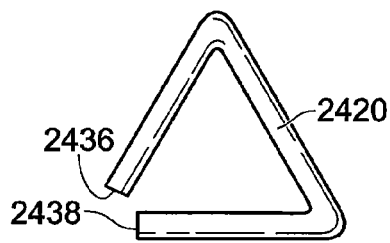
Fig. 24
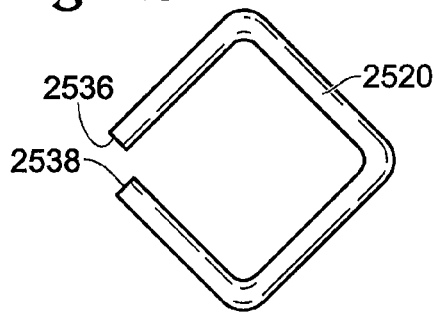
Fig. 25
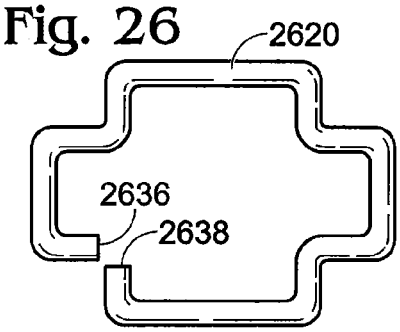
Fig. 26
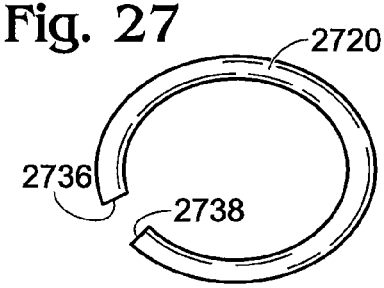
Fig. 27
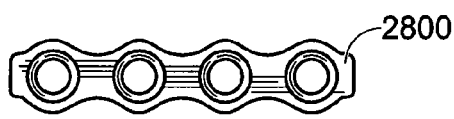
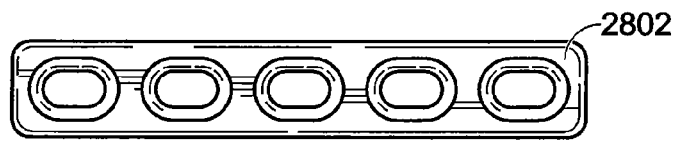
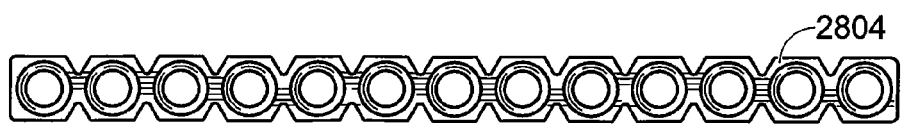
Fig. 28 (PRIOR ART)

LOW PROFILE MEDICAL LOCKING PLATE AND BONE SCREW DESIGN FOR BONE FRACTURES

FIELD

The present disclosure relates to devices for bone fracture fixation, and more specifically, to bone plates for stabilization and/or compression of bone fractures.

BACKGROUND

The repair of some bone fractures requires the use of implantable bone plate and screw systems in order to hold pieces of a fractured bone together and/or promote healing of the fracture. FIG. 1 illustrates one example of a conventional bone plate 100 having a plurality of through-holes 102. As shown in FIG. 2, screws 104 can be inserted through the holes 102 in order to be threaded into the bone 106, thereby securing the bone plate 100 to a bone 106 in need of repair. In this manner, the bone plate 100 can be compressed against the bone 106 and the bone fracture can be stabilized.

Conventional bone plate and screw systems promote healing of a fracture by compressing the fracture ends together and drawing the bone fragments into close apposition with each other. Generally, bone plates can be provided with several holes and/or slots, the holes and slots either being threaded or non-threaded screw holes, depending on the type of screw being used.

Threaded screw holes (e.g., through-holes in the bone plate with internal threads) are conventionally used with specialized screws having a threaded head portion in addition to a threaded shaft. These screws are typically referred to as "locking" screws. The threaded head portion engages with the threads of the screw hole to form a locking bone plate system (e.g., the locking screw is threaded into both the bone plate and the bone). Locking screws must be inserted at a fixed, predetermined angle with respect to the bone plate, such angle being determined by the central axis of the threaded hole. Once inserted, locking screws resist loosening and ensure stability between the screw and bone plate.

Non-threaded screw holes are conventionally used with standard screws (e.g., screws with non-threaded heads). These standard screws do not lock with the bone plate and are typically referred to as "non-locking" screws. Non-locking screws can be inserted at various different angles through the bone plate screw holes, depending on the requirements of the specific application.

Disadvantages exist with both types of bone plate through-holes. For example, non-locking screws may loosen in response to micromotion of the bone reconstruction. Stable bone fixation is critical to avoid delayed healing, non-union of the fracture, and potential implant failure from screw loosening or screw breakage. Thus, non-locking screws are susceptible to these and other disadvantages.

On the other hand, locking screws are specialized screws, and much more costly than standard bone screws (with a non-threaded head). Standard bone screws can be used with threaded screw holes in order to create a locking bone plate system, however, such systems often require a bone plate height of 5 mm or greater (0.198 inches or greater) in order to provide space for accommodating the bone screw head and for enough threads to engage the bone screw shaft. Bone plates having a height of 5 mm or greater are disadvantageous because such heights may make it difficult for a surgeon to close the wound over the bone plate. For example, suturing the skin closed over a bone plate with a 5 mm height may impose extra tension on the skin and soft tissues, potentially resulting in complications such as non-healing and/or infection.

There thus remains a need for an improved bone plate and bone screw system that can provide a locking relationship while reducing or eliminating the above-described disadvantages.

SUMMARY

Disclosed embodiments of a bone plate and screw system can allow for a locking relationship between the bone plate and bone screw, with the use of a standard (non-threaded head) bone screw. Furthermore, disclosed embodiments can provide for a locking bone plate having a low profile (e.g., a height of less than about 5 mm). Some embodiments include a bone plate having non-threaded screw-holes and screws having non-threaded heads.

One embodiment of a bone plate comprises a bone-contacting surface, a second surface opposite the bone-contacting surface, defining a plate thickness therebetween, at least one non-threaded through-hole passing between the bone-contacting surface and the second surface, said through-hole being configured to receive a bone screw, and a locking element, wherein said locking element is configured to engage a thread of the bone screw, and wherein a first end of the locking element is coupled to the bone plate. For example, the first end of the locking element can be secured to the bone-contacting surface of the bone plate and/or the locking element can be secured to the plate thickness.

Some embodiments comprise a flange arranged within the through-hole. The flange can be positioned substantially centrally along the plate thickness. In other embodiments, the flange can be positioned adjacent the bone-contacting surface. Some embodiments comprise a second flange that can be positioned, for example, adjacent the second surface of the bone plate. Additionally or alternatively, some embodiments can comprise a counter-bore recess adjacent the bone-contacting surface of the bone plate. In some embodiments, the counter-bore recess can substantially prevent migration of the locking element towards the second surface of the bone plate.

In some embodiments, the through-hole can comprise a tapered portion to accommodate a head of the bone screw. For example, the tapered portion can be configured to allow substantially the entire head of the bone screw to be positioned between the bone-contacting surface and the second surface. In some embodiments, the through-hole can comprise a chamfered and/or counter-sunk portion. In this manner, the hole opening adjacent the second surface of the bone plate can be configured to engage with the head of the bone screw.

The flange and/or the locking element can be arranged to provide a concentric opening within the screw-hole. In some embodiments, the diameter of the concentric opening can be larger than a minor diameter of the bone screw and smaller than a major diameter of the bone screw (e.g., the diameter of the concentric opening can be greater than the root diameter of the bone screw shaft and less than the outer diameter of the bone screw threads). In some embodiments, the concentric opening can be substantially circular. The flange can have a flange thickness less than a pitch of a thread of the bone screw in some embodiments. In some embodiments, the cross-sectional diameter of the locking element can be less than a pitch of a thread of the bone screw.

The locking element can take many possible forms in different embodiments. For example, the locking element can comprise a straight wire. In some embodiments, the straight wire can comprise a first end, a second end, and a central portion between the first and second ends, wherein the first and second ends are welded to the bone plate (e.g., to the bone-contacting surface and/or to the counter-bore recess) or within the plate thickness and the central portion extends transversely across the through-hole. In some embodiments, the central portion can be curved.

Embodiments of the locking element can comprise, for example, a coil spring, a straight wire, two straight wires arranged substantially parallel to one another, a substantially triangular wire, a substantially square wire, and/or a substantially circular wire.

In some embodiments, the through-hole can be tapered to allow for angulation of the bone screw.

According to one embodiment, a bone plate can comprise a bone-contacting surface, a second surface opposite the bone-contacting surface, defining a plate thickness therebetween, at least one non-threaded through-hole passing between the bone-contacting surface and the second surface, a flange formed integrally with the through-hole, and a head-engaging portion configured to engage a head of a bone screw inserted into the through-hole, wherein the head engaging portion and the flange are configured to form a locking relationship between the bone plate and the bone screw.

In some embodiments, the head-engaging portion can comprise a chamfered, tapered, or countersunk portion adjacent the second surface. In some embodiments, the head-engaging portion can comprise a thin wall formed between the through-hole and one or more adjacent bores, between the through-hole and an annular channel surrounding the through-hole, and/or between the through-hole and one or more longitudinal slits formed in the plate thickness, extending from the second surface towards the bone-contacting surface.

According to some embodiments, the flange can be positioned adjacent the bone-contacting surface. The head-engaging portion can comprise a second flange positioned adjacent the second surface of the bone plate.

In some aspects, the through-hole can be configured to allow insertion of the bone screw from either the bone-contacting surface or the second surface.

Some embodiments can comprise a locking element positioned at least partially within an opening formed by the flange, the locking element being configured to engage threads of the bone screw.

The bone plate can be a low profile bone plate, having a thickness of less than about 5 mm.

The present disclosure also concerns methods for providing a locking relationship between a bone plate and a bone screw inserted into a non-threaded through-hole provided in the bone plate. One embodiment of a method can comprise forming a concentric opening within the through-hole, the concentric opening having a diameter that is greater than a minor diameter of the bone screw and less than a major diameter of the bone screw, inserting a bone screw into the through-hole and concentric opening, tightening the bone screw so as to engage threads of the bone screw with the concentric opening, engaging a head of the bone screw with a head-engaging portion of the bone plate, and tightening the bone screw further such that the bone screw head compresses the head-engaging portion and the threads compress against the concentric opening, thereby forming a locking relationship between the bone screw and the bone plate.

In some embodiments, forming a concentric opening comprises providing a flange formed integrally with the through-hole. Forming a concentric opening can comprise providing a locking element positioned within the through-hole.

According to some embodiments, providing a locking element can comprise positioning one or more of a straight wire, a curved wire, a looped wire, and a coil spring within the through-hole.

In some methods, the concentric opening can be positioned adjacent a bone-contacting surface of the bone plate, and the head-engaging portion can be positioned adjacent a second surface of the bone plate opposite the bone-contacting surface.

Some methods can include providing a counter-bore recess adjacent a bone-contacting surface of the bone plate. Further, a locking element having a first end can be provided, and the first end of the locking element can be welded to the counter-bore recess, thereby substantially preventing movement of the locking element during tightening of the bone screw.

The foregoing and other objects, features, and advantages of the invention will become more apparent from the following detailed description, which proceeds with reference to the accompanying figures.

BRIEF DESCRIPTION OF THE DRAWINGS

FIG. 4 illustrates a section view of one embodiment of a bone plate through-hole.

FIG. 5 illustrates a section view of one embodiment of a bone plate through-hole.

FIG. 6 illustrates a section view of one embodiment of a bone plate through-hole.

FIG. 7 illustrates a section view of one embodiment of a bone plate through-hole, taken along line 7-7 in FIG. 29.

FIG. 12 illustrates a top view of the bone plate through-hole of FIG. 11, along line 12-12.

FIG. 13 illustrates a section view of a spring coil locking element within a bone plate through-hole.

FIG. 14 illustrates a top plan view of a spring coil locking element.

FIG. 15 illustrates a side elevation view of a spring coil locking element.

FIG. 16 illustrates a perspective view of a spring coil locking element within a bone plate through-hole.

FIG. 17 illustrates a cut away perspective view of a spring coil locking element around a bone screw in a bone plate through-hole.

FIG. 18 illustrates a section view of an angled bone screw in a bone plate through-hole with a spring coil locking element.

FIG. 19 illustrates a top plan view of one embodiment of a locking element within a bone plate through-hole.

FIG. 20 illustrates a top plan view of one embodiment of a locking element within a bone plate through-hole.

FIG. 21 illustrates a top plan view of one embodiment of a locking element within a bone plate through-hole.

FIG. 22 illustrates a top plan view of one embodiment of a locking element within a bone plate through-hole.

FIG. 23 illustrates a top plan view of one embodiment of a locking element within a bone plate through-hole.

FIG. 24 illustrates a top plan view of one embodiment of a locking element.

FIG. 25 illustrates a top plan view of one embodiment of a locking element.

FIG. 26 illustrates a top plan view of one embodiment of a locking element.

FIG. 27 illustrates a top plan view of one embodiment of a locking element.

FIG. 28 illustrates a top plan view of various prior art bone plates.

FIG. 29 is a perspective view of the bone plate through-hole of FIG. 7.

DETAILED DESCRIPTION

Figure 1:
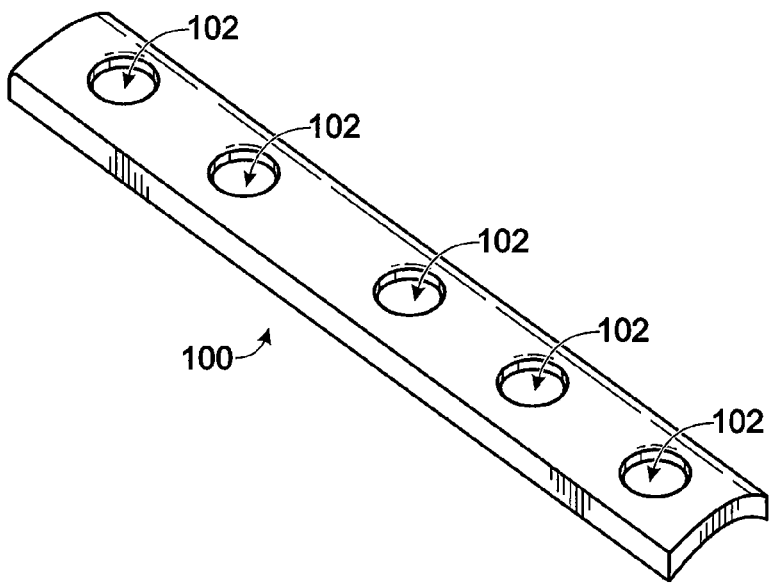
FIG. 1 illustrates a perspective view of a prior art bone plate.
Figure 2:
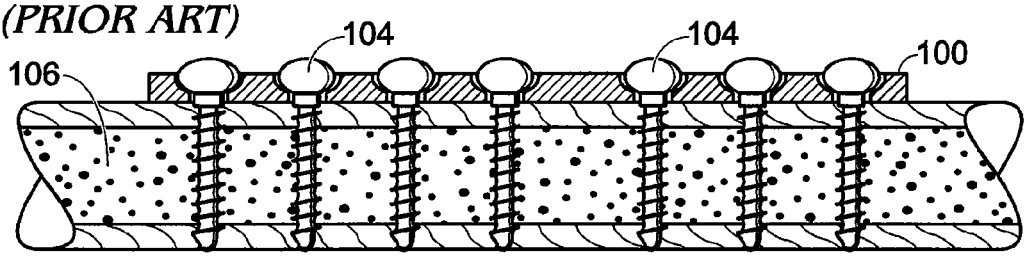
FIG. 2 illustrates a section view of a prior art bone plate secured to a bone segment using bone screws.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled items.

Terms such as "above," "upper," "below," and "lower" are meant only to show the position of some features relative to others as shown in the drawings, and do not necessarily correlate to actual positions or directions of those features when the replacement valve is being delivered and/or is in its implanted configuration or position.

Descriptions and disclosures provided in association with one particular embodiment are not limited to that embodiment, and may be applied to any embodiment disclosed.

Moreover, for the sake of simplicity, the figures may not show the various ways (readily discernable, based on this disclosure, by one of ordinary skill in the art) in which the disclosed system, method, and apparatus can be used in combination with other systems, methods, and apparatuses.

While FIGS. 3-9 show only partial views of bone plates and only one through-hole is visible, a bone plate can include a plurality of through-holes arranged in any suitable fashion. In embodiments with more than one through-hole, each through-hole can be designed substantially the same. In some embodiments, one or more of the through-holes in a given bone plate can have a different design than one or more other through-holes in the bone plate. Such configurations can be optimized for particular applications. As will be described in further detail, embodiments of through-holes can include a hole opening near an upper bone plate surface that has a geometry that engages a standard bone screw head through interference. A flange and/or locking element adjacent a lower surface (e.g., a bone contacting surface) of the bone plate can be provided to work with the hole opening geometry to effectively lock a bone screw in place, once tightened.

Figure 3:
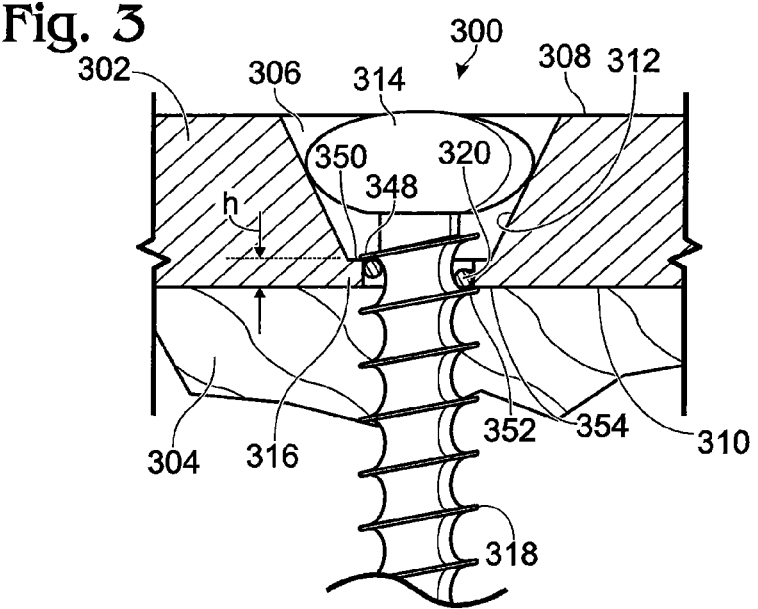
FIG. 3 illustrates a section view of a non-threaded locking through-hole according to the present disclosure.

FIG. 3 illustrates a section view of one embodiment of a low profile locking bone plate according to the present disclosure. A screw 300 can be used to secure a bone plate 302 (e.g., a low profile bone plate) to a portion of a bone 304. The screw 300 can be a standard bone screw 300, without a threaded head, and having a constant root diameter. Through-hole 306 can pass through the entire plate thickness of the bone plate 302, from a bone contacting surface 310 to a second surface 308. Through-hole 306 can be provided with, for example, a tapered or angled side wall 312, against which the head 314 of the bone screw 300 can be compressed. Thus, the side wall 312 can be a head-engaging portion in some embodiments.

Through-hole 306 can also include a flange 316 (e.g., an annular flange) that can engage with the threads 318 of the bone screw 300. Flange 316 can be formed integrally with the through-hole 306. Flange 316 can create an opening concentric with the through-hole 306, where the concentric opening has a diameter that is less than the major diameter of the bone screw 300 and greater than the minor diameter of the bone screw 300. Additionally, the height h of flange 316 can be less than the pitch of the threads 318. In this manner, the bone screw 300 can be screwed into the bone 304, by being screwed through the flange 316. As the screw 300 is tightened and the head 314 engages with the side wall 312, a first portion 348 of the thread 318 can engage with an upper surface 350 of the flange 316. Furthermore, as the screw 300 is tightened, a second portion 352 of the thread 318 can engage with a lower surface 354 of the flange 316.

In some embodiments, the through-hole 306 can include a locking element 320. Locking element 320 can be, for example, a straight wire or a spring coil, as will be described in further detail below, in association with FIGS. 11-27. The locking element 320 can create an opening (e.g., an opening concentric with the through-hole 306) having a diameter that is less than the major diameter of the bone screw 300 and greater than the minor diameter of the bone screw 300. As the bone screw 300 is tightened into the bone 304, the locking element 320 can flex, thereby improving the lock between the bone screw 300 and the bone plate 302. As the bone screw head 314 engages with the hole opening adjacent the second surface 308 of the bone plate 302 (e.g., the tapered side walls 312 of the through-hole 306), the locking element 320 can be compressed between the threads 318 and the flange 316. In some embodiments, as the screw 300 is tightened and the screw head 314 is compressed against the side wall 312 near the hole opening at the first surface 308 of the bone plate 302, the locking element 320 can be tensioned between the threads 318 and the bone plate 302.

The locking element 320 can be positioned adjacent the bone-contacting surface 310 of bone plate 302, with at least one end secured to the bone plate 302 to substantially prevent the locking element 320 from rotating or moving relative to the screw 300 as the screw 300 is inserted and tightened. For example, at least one end of the locking element 320 can be laser welded to the bone plate 302 (e.g., laser welded to the bone-contacting surface 310, to the flange 306, and/or to the plate thickness).

While FIG. 3 illustrates a locking element 320, locking element 320 is optional. Furthermore, while the through-holes illustrated in FIGS. 4-9 are not shown with locking elements, each of these embodiments can include one or more locking elements (any of the locking elements described above or below), such locking elements being further described below.

FIGS. 4-9 illustrate various other embodiments of a through-hole having a flange that can be included in a bone plate.

FIG. 4 shows another embodiment of a bone screw 400 securing a bone plate 402 to a bone 404 and having a bone screw head 414. Bone screw 400 can be a standard bone screw, without a threaded head. Bone plate 402 can include a through-hole 406 that passes from a first surface 408 to an opposite, bone-contacting surface 410. Through-hole 406 can include substantially straight side walls 412 and a flange 416. Flange 416 can be formed integrally with the through-hole 406. The flange 416 can have a height h that is less than the pitch of threads 418 of bone screw 400. Furthermore, the flange 416 can create a concentric opening within the through-hole 306, the opening having a diameter that is less than the major diameter of the bone screw 400, and greater than the minor diameter of the bone screw 400.

FIG. 5 shows another embodiment of a bone screw 500 securing a bone plate 502 to a bone 504. Bone screw 500 can be a standard bone screw, without a threaded head. Bone plate 502 can include a through-hole 506 that passes from a first surface 508 to an opposite, bone-contacting surface 510. Through-hole 506 can include substantially straight side walls 512 and a chamfered portion 522 adjacent the first surface 508. The chamfered portion 522 can be sized relative to the bone screw head 514 such that a portion of the bone screw head 514 is positioned outside of the through-hole 506 (e.g., above the first surface 508 of the bone plate 502) when the bone screw 500 is locked with the bone plate 502 (e.g., when the bone screw 500 is fully inserted into the bone 504). Thus, the chamfered portion 522 can be a head-engaging portion. Through-hole 506 can also include a flange 516 that can be formed integrally with the through-hole 506. The flange 516 can have a height h that is less than the pitch of threads 518 of bone screw 500. Furthermore, the flange 516 can create an opening having a diameter that is less than the major diameter of the bone screw 500, and greater than the minor diameter of the bone screw 500.

FIG. 6 shows another embodiment of a bone screw 600 securing a bone plate 602 to a bone 604. Bone screw 600 can be a standard bone screw, without a threaded head. Bone plate 602 can include a through-hole 606 that passes from a first surface 608 to an opposite, bone-contacting surface 610. Through-hole 606 can include substantially straight side walls 612 and a curved, countersunk portion 624 adjacent the first surface 608. The countersunk portion 624 can be, for example, a spherical countersink. The countersunk portion 624 can be sized relative to the bone screw head 614 such that substantially all of the bone screw head 614 is positioned within the through-hole 606 (e.g., below the first surface 608 of the bone plate 602) when the bone screw 600 is locked with the bone plate 602 (e.g., when the bone screw 600 is fully inserted into the bone 604). Thus, the countersunk portion 624 can be a head-engaging portion. Through-hole 606 can also include a flange 616 that can be formed integrally with the through-hole 606. The flange 616 can have a height h that is less than the pitch of threads 618 of bone screw 600. Furthermore, the flange 616 can create an opening having a diameter that is less than the major diameter of the bone screw 600, and greater than the minor diameter of the bone screw 600.

FIG. 7 shows an embodiment of a bone plate 702 having a through-hole 706. As shown in FIG. 7, a bone screw 700 can secure a bone plate 702 to a bone 704. Bone screw 700 can be a standard bone screw, without a threaded head. Bone plate 702 can include a through-hole 706 that passes from a first surface 708 to an opposite, bone-contacting surface 710. Through-hole 706 can include substantially straight side walls 712, a chamfer 734, and a flange 716 that can be formed integrally with the through-hole 706. The flange 716 can have a height h that is less than the pitch of threads 718 of bone screw 700. Furthermore, the flange 716 can create an opening having a diameter that is less than the major diameter of the bone screw 700, and greater than the minor diameter of the bone screw 700.

As also seen in FIG. 29, bone plate 702 can also include an annular channel 729 surrounding the through-hole 706. In one embodiment, the annular channel 729 can extend from the first surface 708 towards the bone-contacting surface 710, but does not pass all the way through the thickness of the bone plate 702. The annular channel 729 can create thin walls 728 in the bone plate 702 that deflect or flex under pressure from the bone screw head 714 as the bone screw 700 is tightened into the bone 704. In this manner, the deformation of the thin walls 728 can lock the bone screw 700 against the bone plate 702. The thin walls 728 can thus be head-engaging portions of the bone plate 702. In some embodiments, one or more slots or bores 726 can be positioned adjacent one or more through-holes 706. For example, one or more bores can be formed in the thin wall 728 such that the thin wall 728 is configured as a sectioned annular ring surrounding the through-hole 706, as seen in FIG. 29. In the embodiment of FIG. 29, four bores 726 are spaced at substantially 90 degree intervals around the through-hole 706. In other embodiments, more or fewer bores 726 can be provided, spaced at different intervals. In some embodiments, the thin wall 728 can be a solid annular ring, without any bores 726.

An annular channel 729 can be positioned adjacent each through-hole 706 in the bone plate 702. Alternatively, some through-holes 706 can be positioned without an annular channel 729 in immediate proximity, while other through-holes 706 can be positioned near an annular channel 729.

Figure 8:
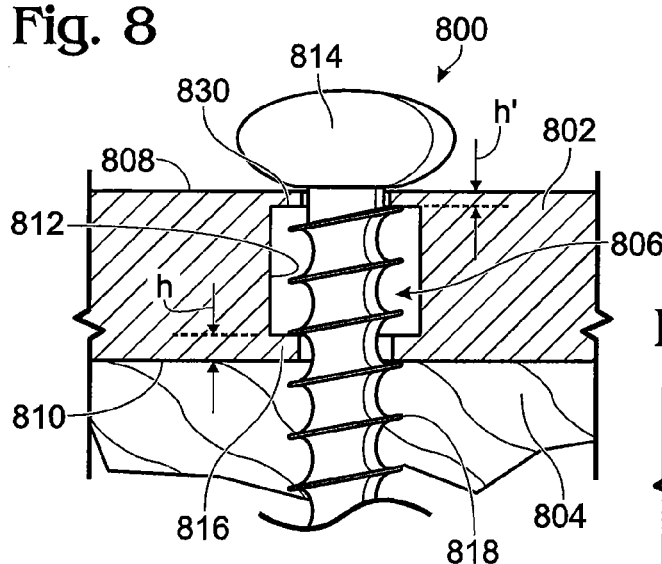
FIG. 8 illustrates a section view of one embodiment of a bone plate through-hole.

FIG. 8 shows an embodiment of a bone plate 802 having a through-hole 806 with a first flange 816 adjacent the bone-contacting surface 810 and a second flange or lip 830 adjacent the first surface 808. The first flange 816 and/or the second flange 830 can be formed integrally with the through-hole 806. As shown in FIG. 8, a bone screw 800 can secure a bone plate 802 to a bone 804. Bone screw 800 can be a standard bone screw, without a threaded head. Bone plate 802 can include a through-hole 806 that passes from a bone plate first surface 808 to an opposite, bone-contacting surface 810. Through-hole 806 can include substantially straight side walls 812 between the first flange 816 and the second flange 830. The flanges 816, 830 can have a height h, h' respectively, each of which can be less than the pitch of threads 818 of bone screw 800. Furthermore, the flanges 816, 830 can create openings concentric with the through-hole, each opening having a diameter that is less than the major diameter of the bone screw 800, and greater than the minor diameter of the bone screw 800. In this manner, the bone screw 800 can be screwed through each of the flanges 816, 830.

The second flange 830 can be sized such that the bone screw head 814 cannot enter the through-hole 806 because the diameter of the opening created by flange 830 can be less than the diameter of the bone screw head 814. Thus, substantially all of the bone screw head 814 can be positioned adjacent the first bone plate surface 808, outside of the through-hole 806. The second flange 830 can be sized such that its thickness allows inward deformation (e.g., deflection of second flange 830 towards the interior of the through-hole 806) of the second flange 830 as the screw 800 is tightened. This deformation of the second flange 830 can further secure the lock between the bone screw 800 and the bone plate 802 as the bone screw is tightened. The second flange 830 can thus be a head-engaging portion of the bone plate 802.

Figure 9:
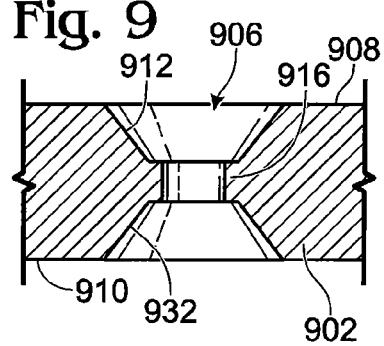
FIG. 9 illustrates a section view of one embodiment of a bone plate through-hole.

FIG. 9 shows a bone plate 902 having a through-hole 906 that can allow for insertion of a bone screw from either side of the bone plate 902. For example, a bone screw can be inserted from the first surface 908 or from the second surface 910. Through-hole 906 can include a first tapered, or angled side wall 912 and a second angled side wall 932, each being configured to receive a bone screw head (thus each being configurable as a head-engaging portion). Side wall 912 and/or side wall 932 can include chamfered portions adjacent the first surface 908 or second surface 910, respectively, such chamfered portions being configured to receive and engage a portion of a bone screw head. Through-hole 906 can also include a flange 916 that can be formed integrally with the through-hole 906. In some embodiments, flange 916 can be substantially centrally located along the thickness of the bone plate 902 (e.g., the flange 916 can be substantially equidistant from the first surface 908 and the second surface 910). In other embodiments, the flange 916 can be closer to the first surface 908 or closer to the second surface 910. The flange 916 can create an opening concentric to the through-hole 906, the opening having a diameter greater than a minor diameter of a bone screw to be inserted, and less than a major diameter of the bone screw. Furthermore, as with other embodiments discussed above, the thickness, or height, of the flange 916 can be less than the pitch of the bone screw threads. The flange 916 can thus engage the threads of the bone screw as the bone screw head engages with the side walls 912 or 932, thereby locking the bone screw in place in the bone plate 902.

FIGS. 11-27 illustrate various embodiments of locking elements that can be used in a through-hole in a bone plate, with or without a flange, in order to create a locking relationship between the bone plate and the bone screw that can substantially prevent the bone screw from loosening over time in some embodiments.

Figure 11:
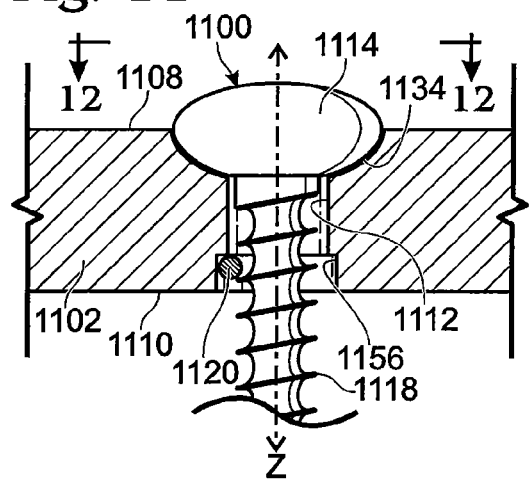
FIG. 11 illustrates a section view of one embodiment of a locking element in place in a bone plate through-hole.

FIGS. 11-12 illustrate one embodiment of a locking element 1120 that can be coupled to a bone plate 1102, and positioned such that at least a portion of the locking element 1120 passes transversely through a through-hole 1106 (FIG. 12). For example, the through-hole 1106 can define a longitudinal axis Z (FIG. 11) through the center of the through-hole 1106, passing from the first surface 1108 of the bone plate 1102 to the second surface 1110. In such an embodiment, the locking element 1120 can be positioned substantially perpendicularly to the longitudinal axis Z. Locking element 1120 can be arranged adjacent the side wall 1112 of the through-hole 1106 such that it is positioned between the side wall 1112 and a bone screw 1100 when the bone screw 1100 is screwed into the bone (bone screw 1100 is not shown in FIG. 12, for clarity).

A first end 1136 and/or a second end 1138 of the locking element 1120 can be secured to the bone plate 1102. For example, in one embodiment, the first end 1136 of the locking element can be welded (e.g., laser welded) to the bone plate 1102 (e.g., welded to the bone-contacting surface 1110 or welded within the bone plate thickness). Thus, the locking element 1120 can remain substantially stationary while a bone screw 1100 is screwed into bone via the through-hole 1106. The cross-sectional diameter of the locking element 1120 can be less than the pitch of the bone screw threads 1118 so that the locking element 1120 can pass between the threads 1118 as the screw 1100 is inserted. The through-hole 1106 can also include a chamfered or countersunk portion 1134 that can accommodate at least a portion of the bone screw head 1114.

The locking element 1120 can be positioned adjacent the bone-contacting surface 1110. In some embodiments, bone plate 1102 can include a counter bore recess 1156 that can substantially prevent the locking element 1120 from advancing towards the head 1114 of screw 1100 as the screw 1100 is tightened. After the screw head 1114 is compressed against the hole opening adjacent the first surface 1108 of the bone plate 1102, as the screw 1100 is further tightened, the locking element 1120 is tensioned and compressed against the recess 1156, thereby locking the screw 1100 in place. In some embodiments, at least one of the ends 1136, 1138 can be secured, such as by laser welding, to a portion of the counter bore recess 1156.

As shown in FIGS. 11-12, the locking element 1120 can be a substantially straight wire. In other embodiments, such as the specific examples shown in FIGS. 13-27, a locking element can be configured in different shapes. For example, a locking element 1320 can be configured as a spring coil 1320, as shown in FIGS. 13-17. Locking element 1320 can include first and second free ends 1336, 1338 being arranged at least slightly offset from one another, as best seen in FIG. 15.

Bone plate 1302 can have a bone-contacting surface and a second surface 1308. The locking element 1320 can be positioned within a through-hole 1306. In some embodiments, locking element 1320 can be positioned adjacent a bone-contacting surface 1310. Bone plate 1302 can include a counter bore recess 1356 that can substantially prevent the locking element 1320 from advancing towards the head 1314 of a screw 1300 as the screw is tightened. Bone plate 1302 can also include a countersink 1334 (with a side wall 1312) to engage the head 1314 of the screw 1300. Locking element 1320 can create an opening concentric to the through-hole 1306, the concentric opening having a diameter d (FIG. 14), through which the screw 1300 can be advanced. The diameter d can be greater than the minor diameter of the screw 1300 and less than the major diameter of the screw 1300. Furthermore, the cross-sectional diameter t of the locking element 1320 can be less than the pitch of the threads 1318, so as not to interfere with tightening of the screw 1300. As shown in FIG. 16, the locking element 1320 can be positioned within a through-hole 1306 so as to engage with the threads 1318 of a screw 1300, inserted as shown in FIG. 17.

Further embodiments of locking element configurations are illustrated in FIGS. 19-23, which show top views of a bone plate through-hole having one or more locking elements positioned transversely across the through-hole. In each of the described embodiments, the one or more locking elements can be secured, for example, to the lower surface of the bone plate (e.g., laser welded to the bone-contacting surface of the bone plate). Each locking element can be provided within a counter bore recess adjacent the bone-contacting surface of the bone plate, as best seen in FIG. 11.

The bone plate 1902 of FIG. 19 can include a through-hole 1906 with chamfered portion 1934 (shown as chamfered portion 2034 in FIG. 20, chamfered portion 2134 in FIG. 21, and chamfered portion 2234 in FIG. 22). Two locking elements 1920 can be positioned to pass across opposing sides of the through-hole 1906. Locking elements 1906 can be substantially straight wires with centrally located bowed or curved portions 1921 exposed in the through-hole 1906. One or both of the ends 1936, 1938 of the locking elements 1920 can be secured (e.g., welded) to the bone plate 1902. FIG. 20 illustrates a similar locking element 2020 to that shown in FIG. 19, but with a single curved locking element 2020 with a bowed or curved portion 2021 instead of two passing across the through-hole 2006. As with the embodiment shown in FIG. 19, one or both of the ends 2026, 2038 of the locking element 2020 can be fixed with respect to the bone plate 2002.

The locking element 2120 shown in FIG. 21 can be provided with just a first end 2136 secured within the bone plate 2120. The second end 2138 of the locking element 2120 can be a free end 2138 positioned within the through-hole 2106. The portion 2121 of the locking element 2120 arranged within the through-hole 2106 can be configured to form a substantially circular, concentric coil shape as seen in FIG. 21. In this configuration, there can be more surface contact between the locking element 2120 and a bone screw inserted into the through-hole 2106. The curved portion 2121 of the locking element can be configured substantially concentrically within the through-hole 2106, so as not to interfere with insertion of the bone screw. The locking element 2120 can thus create an opening concentric with the through-hole 2106, the opening having a diameter greater than the minor diameter of a bone screw inserted into the through-hole 2120 and less than the major diameter of the bone screw. In some embodiments, the through-hole 2106 can be provided with a counter bore recess that would substantially obscure vision of the locking element 2120 in the view seen in FIG. 21.

FIG. 22 shows another embodiment of a locking element 2220 that can be provided in a through-hole 2206 of a bone plate 2202. Locking element 2220 can include a first end 2236 and a second end 2238. First end 2236 and second end 2238 can each be positioned within the thickness of bone plate 2202, and either or both of the first and second ends 2236, 2238 can be secured (e.g., welded) to or within the bone plate 2202. Locking element 2220 can include a central portion 2240 arranged in a coiled configuration in the through-hole 2206. As shown in FIG. 22, the central portion 2240 can be arranged such that the central axis of the coiled central portion 2240 is perpendicular to the longitudinal axis of through-hole 2206. Central portion 2240 can include four direction changes to create the coil, as seen in FIG. 22. Alternatively, the coil can include more or fewer direction changes.

FIG. 23 shows another embodiment of a locking element 2320 that can be provided in a through-hole 2306 of a bone plate 2302. Locking element 2320 can include a first end 2336 and a second end 2338. First end 2336 and second end 2338 can each be positioned within the thickness of bone plate 2302, and either or both of the first and second ends 2336, 2338 can be secured (e.g., welded) to or within the bone plate 2302. In other embodiments, first and/or second ends 2336, 2338 can be coupled to the bone-contacting surface of bone plate 2302. Locking element 2320 can include a central portion 2340 arranged in a looped configuration in the through-hole 2306. As shown in the example seen in FIG. 23, the looped central portion 2340 can be arranged such that a first segment 2342 crosses over a second segment 2344, which continues to the second end 2338. The looped portion 2340 can create an opening within the through-hole 2306, the opening having a diameter greater than the minor diameter of a bone screw inserted in the through-hole 2306, and less than the major diameter of the bone screw. As the bone screw is tightened, the bone screw head can engage with chamfered or countersunk portion 2334, while the bone screw threads engage with the locking element 2320 to lock the bone screw in place with respect to the bone plate 2302.

In addition to the above-described embodiments of various locking elements, other configurations are also suitable. For example, FIGS. 24-27 illustrate additional embodiments of possible locking elements 2420, 2520, 2620, and 2720, respectively. Each of the embodiments shown in FIGS. 24-27 can be incorporated into or across a through-hole of a bone plate, as described above. FIG. 24 shows a locking element 2420 that can be arranged in a substantially triangular configuration. FIG. 25 shows a locking element 2520 that can be arranged in a substantially square or diamond configuration. FIG. 26 shows a locking element 2620 that can be arranged in a polygonal configuration, such as the substantially cross-shaped configuration shown. FIG. 27 shows a locking element 2720 that can be arranged in a substantially elliptical or oval configuration. Each of the embodiments can have two free ends 2436, 2438, 2536, 2538, 2636, 2638, 2736, 2738, respectively. In alternative embodiments, one or more of the free ends can be secured (e.g., laser welded) to a bone plate.

Figure 10:
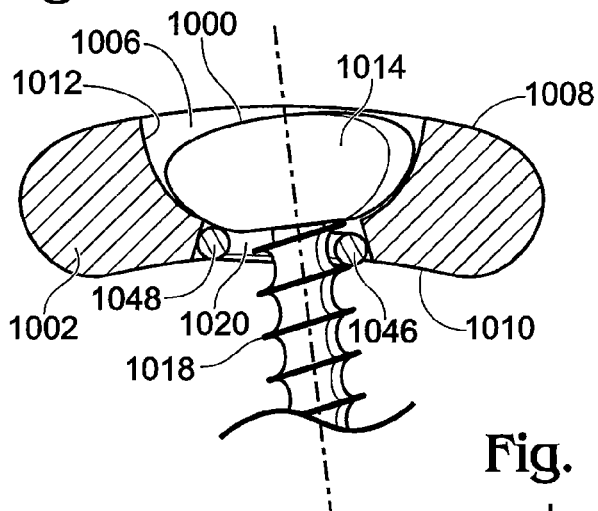
FIG. 10 illustrates a section view of one embodiment of a bone plate through-hole with a bone screw inserted at an angle to the through-hole axis.

Disclosed embodiments can allow for angulated insertion of a bone screw into a bone plate, as shown in FIGS. 10 and 18. FIG. 10 shows a bone plate 1002 having a through-hole 1006 that can allow for angulated insertion of bone screw 1000. As shown in FIG. 10, side walls 1012 of the through-hole 1006 can be curved and enlarged with respect to the bone screw head 1014, in order to facilitate adjustment of the bone screw 1000 so that it can be inserted into a bone segment at any angle within a range of angles. Side walls 1012 can engage the head 1014 of the bone screw 1000 no matter the angle of insertion.

Through-hole 1006 can include a locking element 1020 that can provide a locking relationship between the bone plate 1002 and the bone screw 1000 without requiring a threaded bone screw head 1014 or other specialized bone screw features (e.g., the bone screw 1000 can have a constant diameter shaft). For example, the locking element 1020 can engage with the threads 1018 of the bone screw 1000. As shown in FIG. 10, when a bone screw 1000 is inserted at an angle relative to the longitudinal axis of the through-hole 1006, a first portion 1046 of the locking element 1020 may engage with the threads 1018, while a second portion 1048 of the locking element 1020 may be spaced apart from the threads 1018, due to the angulation of the bone screw 1000. Additionally or alternatively, through-hole 1006 can be provided with a flange positioned adjacent the first surface 1008, the second surface 1010, and/or between the first and second surfaces 1008, 1010, such as substantially centrally located between the two surfaces.

FIG. 18 shows another embodiment of a bone plate 1802 having a through-hole 1806 that can accommodate a bone screw 1800 inserted at an angle with respect to the longitudinal axis Z of the through-hole 1806. Through-hole 1806 can include a countersunk portion 1834 adjacent a first surface 1808 to accommodate at least a portion of the screw head 1814. Through-hole 1806 can also be provided with a locking element 1820, such as coil spring 1820, which can engage the threads 1818 of the bone screw 1800. The locking element 1820 can have a cross-sectional diameter that is less than the pitch of the threads 1818, such that the bone screw 1800 can be threaded through the through-hole 1806 and locking element 1820 until the screw head 1814 engages with the countersunk portion 1834. Through-hole 1806 can also be provided with a widened portion 1840 adjacent a second bone plate surface 1810 that can facilitate angled insertion of the bone screw 1800. To further facilitate angled insertion of a screw 1800, the through-hole 1806 can include tapered side wall 1812.

Figure 30:
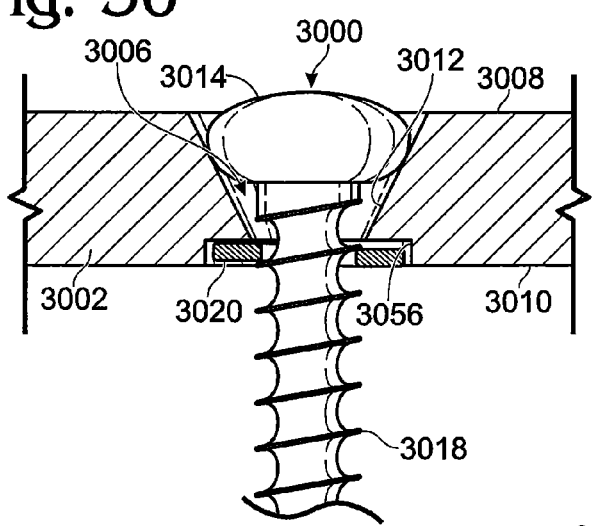
FIG. 30 is a section view of one embodiment of a through-hole having a counter-bore recess according to the present disclosure.
Figure 31:
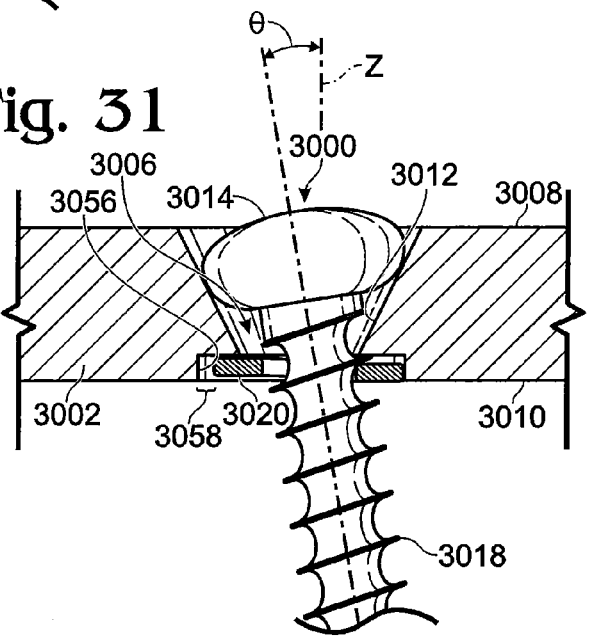
FIG. 31 is a section view of an angled bone screw in a bone plate through-hole with a flattened locking element.
Figure 32:
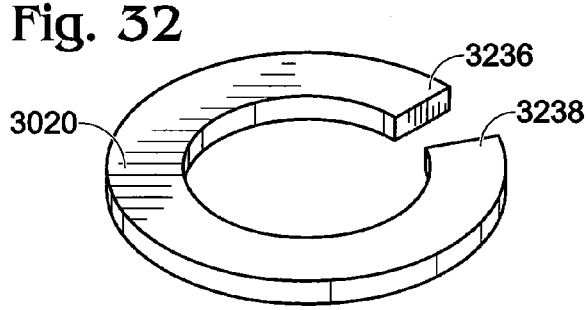
FIG. 32 is a perspective view of one embodiment of a locking element that can be positioned within a bone plate through-hole.
Figure 33:
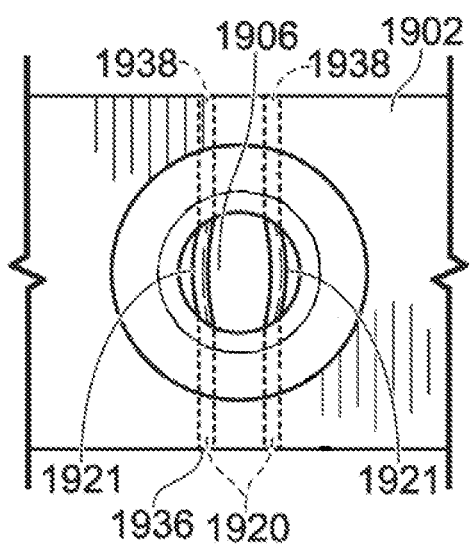
FIG. 33 is a view of the flange having a lower surface that is co-planar with the bone-contacting surface used in combination with the locking element comprising a straight wire.

While the locking elements illustrated and described above generally have a circular cross-section, other cross-section configurations are also suitable for use with any of the embodiments described above or below. For example, locking elements can be provided with elliptical, square, triangular, or any other cross-sectional geometries. One embodiment of a locking element 3020 having a non-circular cross section is shown in FIG. 32. In some embodiments, the locking element 3020 can be a flattened ring, having a substantially rectangular cross section. The locking element can have a first free end 3236 and a second free end 3238. In alternative embodiments, the locking element can have a different cross-sectional geometry, can be a solid ring, and/or can have two free ends offset from one another along the Z axis (the longitudinal axis of the through-hole 3006). In some embodiments, one or both of the free ends 3236, 3238 can be secured to a bone plate 3002 (FIGS. 30-31). For example, one or both of the free ends 3236, 3238 can be welded (e.g., laser welded) to the bone plate 3002, such as to a counter-bore recess 3056.

In some embodiments, a low profile bone plate can include one or more through-holes adapted for insertion of a screw parallel to the longitudinal axis of the through-hole, or insertion at an angle to the longitudinal axis of the through-hole. For example, FIGS. 30-31 illustrate such a through-hole 3006, which can include a locking element 3020. Bone plate 3002 can include one or more through-holes 3006, which form an opening between a first surface 3008 and a bone-contacting surface 3010. The through-hole 3006 can include tapered (e.g., angled) side walls 3012 and can be configured to receive a bone screw 3000. The side walls 3012 can be configured to engage with the head 3014 of the bone screw 3000 as the bone screw 3000 is tightened into a portion of a patient's bone. Through-hole 3006 can also include a counter-bore recess 3056 that can be positioned, for example, adjacent the bone-contacting surface 3010. The counter-bore recess 3056 can, in some embodiments, contain a locking element 3020. Locking element 3020 can be substantially ring shaped, thereby forming an opening (e.g., the inner diameter of the locking element) concentric with the through-hole 3006. The concentric opening can have a diameter that is greater than the minor diameter of the bone screw 3000 and less than the major diameter of the bone screw 3000. Thus, when a bone screw 3000 is inserted into the through-hole 3006 and through the locking element 3020, the locking element 3020 does not prevent the bone screw 3000 from being screwed into the bone, but instead engages with the threads 3018 of the bone screw 3000.

In some embodiments, a portion of the locking element 3020 can engage with the counter-bore recess 3056 as the bone screw 3000 is tightened, with the counter-bore recess 3056 preventing the locking element 3020 from migrating towards the first surface 3008 of the bone plate as the bone screw 3000 is tightened. In some embodiments, at least a portion of the locking element 3020 can be secured to the counter-bore recess 3056. For example, at least one end of the locking element 3020 can be welded to the counter-bore recess 3056.

As shown in FIG. 31, the through-hole 3006 can be enlarged with respect to a normal through-hole size for a given bone screw, in order to allow for insertion of a bone screw 3000 at an angle θ with respect to the longitudinal axis Z of the through-hole 3006. Inserting the bone screw 3000 at an angle θ can cause, or be facilitated by, shifting of the locking element 3020 within the counter-bore recess 3056, to create a gap 3058 between one edge of the locking element 3020 and the bone plate 3002. The locking element 3020 can be designed such that even when it is positioned in this shifted arrangement, its width is such that at least a portion of the locking element 3020 adjacent the gap 3058 is still positioned within the counter-bore recess 3056, thereby preventing migration of the locking element 3020 towards the first surface 3008, even if the bone screw 3000 is inserted at an angle θ.

Bone plates according to the present disclosure can include a plurality of bone screws and screw holes, and can include one or more of any of the illustrated screw-holes with or without flanges, with or without one or more locking elements. In this manner, a low profile bone plate can function as a locking bone plate without the need for specialized bone screws with threaded heads, and without the need for threaded through-holes. However, if desired, any of the described embodiments of through-holes can be threaded, or have threaded portions in addition to the other features described. Any of the described embodiments are amenable to a low-profile bone plate design, as the described bone plates can provide a locking relationship between the bone plate and one or more bone screws without the need for threaded holes or specialized bone screws. Accordingly, any of the described embodiments can be provided in a bone plate having a low-profile, such as a bone plate having a thickness of less than about 5 mm. In some embodiments, a low-profile bone plate according to the present disclosure can have a thickness of from about 0.1 mm to about 5 mm. Specific embodiments of a low-profile bone plate can have a thickness of from about 1 mm to about 5 mm.

Disclosed embodiments of a low profile bone plate can comprise any suitable material. For example, a low profile bone plate can include materials such as stainless steel, titanium, cobalt, chromium, molybdenum, tungsten, nickel, aluminum, vanadium, PMMA, PEEK, ceramics, silicone, PLA, PGA, UHMWPE, polymers, or alloys or combinations thereof. Disclosed low profile bone plates can also be provided with one or more layers of a ceramic, polymer, and/or one or more layers of various other coatings. For example, some embodiments of low profile bone plates can include a porous outer coating. Embodiments of a locking element can also comprise any suitable material. For example, a locking element can include materials such as metal and/or polymer wires, stainless steel, titanium, cobalt, chromium, molybdenum, tungsten, nickel, aluminum, vanadium, PMMA, PEEK, ceramics, silicone, PLA, PGA, UHMWPE, polymers, or alloys or combinations thereof. One specific embodiment of a locking element can comprise stainless steel spring wire.

Any of the disclosed embodiments can be combined or used with one another in any type of bone plate. FIG. 28 illustrates a few examples of different prior art bone plate geometries 2800, 2802, 2804 that can be provided with the through-holes and locking elements herein described. The bone plates shown in FIG. 28 are shown simply as examples, and are not meant to be limiting in any way. Disclosed embodiments of bone plates and through-holes can be incorporated into any type of bone plate, for both human and veterinary applications.

A method for providing a locking relationship between a bone plate and a bone screw inserted into a non-threaded through-hole provided in the bone plate is also disclosed. In some embodiments, a concentric opening can be formed within the through-hole, the concentric opening having a diameter that is greater than a minor diameter of the bone screw and less than a major diameter of the bone screw. A bone screw can be inserted into the through-hole and concentric opening, and tightened. As the bone screw is tightened, the threads of the bone screw can engage with the concentric opening and a head of the bone screw can engage with a head-engaging portion of the bone plate. As the bone screw is tightened, the bone screw head can compress the head-engaging portion and the threads can compress against the concentric opening, thereby forming a locking relationship between the bone screw and the bone plate.

The concentric opening can be formed by providing a flange formed integrally with the through-hole and/or by providing a locking element positioned within the through-hole. The locking element can be any locking element described above, such as a straight wire, a curved wire, a looped wire, and/or a coil spring positioned within the through-hole.

In some embodiments, the concentric opening can be positioned adjacent a bone-contacting surface of the bone plate, and the head-engaging portion can be positioned adjacent a second surface of the bone plate opposite the bone-contacting surface. Some methods include providing counter-bore recess adjacent a bone-contacting surface of the bone plate. In such embodiments, a first end of the locking element can be welded to the counter-bore recess, thereby substantially preventing movement of the locking element during tightening of the bone screw.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A bone plate, comprising:
a bone-contacting surface;
a second surface opposite the bone-contacting surface, defining a plate thickness therebetween;
at least one non-threaded through-hole passing between the bone-contacting surface and the second surface, said through-hole being configured to receive a bone screw;
a locking element, wherein said locking element is configured to engage threads of the bone screw, and wherein a first end of the locking element is coupled to the bone plate; and
an annular flange arranged within the through-hole, the flange having a lower surface that is co-planar with the bone-contacting surface and the locking element extends between a central opening in the annular flange, wherein the locking element comprises a straight wire.
2. The bone plate according to claim 1, wherein the through-hole comprises a tapered portion to accommodate a head of the bone screw.
3. The bone plate according to claim 2, wherein the tapered portion is configured to allow substantially the entire head of the bone screw to be positioned between the bone-contacting surface and the second surface.
4. The bone plate according to claim 1, wherein the through-hole comprises a chamfered portion.
5. The bone plate according to claim 1, wherein the flange is arranged to provide a concentric opening within the through-hole, and wherein the diameter of the concentric opening is larger than a minor diameter of the bone screw and smaller than a major diameter of the bone screw.
6. The bone plate according to claim 5, wherein the concentric opening is substantially circular.
7. The bone plate according to claim 1, wherein the flange has a flange thickness less than a pitch of a thread of the bone screw.
8. The bone plate according to claim 1, wherein the flange is positioned adjacent the bone-contacting surface.
9. The bone plate according to claim 8, further comprising a second flange positioned adjacent the second surface.
10. The bone plate according to claim 1, wherein at least the first end of the locking element is secured to the bone-contacting surface of the bone plate.
11. The bone plate according to claim 1, wherein at least the first end of the locking element is secured within the plate thickness.
12. The bone plate according to claim 1, wherein the straight wire comprises a first end, a second end, and a central portion between the first and second ends, wherein the first and second ends are welded to the bone plate, and the central portion extends transversely across the through-hole.
13. The bone plate according to claim 12, wherein the central portion is curved.
14. The bone plate according to claim 1, wherein the locking element comprises two straight wires arranged substantially parallel to one another.
15. The bone plate according to claim 1, wherein the locking element in configured to be substantially triangular.
16. The bone plate according to claim 1, wherein the locking element is configured to be substantially square-shaped.
17. The bone plate according to claim 1, wherein the locking element is configured to be substantially elliptical.
18. The bone plate according to claim 1, wherein a cross-sectional diameter of the locking element is less than a pitch of a thread of the bone screw.
19. The bone plate according to claim 1, wherein the through-hole is configured to allow for angulation of the bone screw.
20. A bone plate, comprising:
a bone-contacting surface;
a second surface opposite the bone-contacting surface, defining a plate thickness therebetween;
at least one non-threaded through-hole passing between the bone-contacting surface and the second surface, said through-hole being configured to receive a bone screw;
a locking element, wherein said locking element is configured to engage threads of the bone screw, and wherein a first end of the locking element is coupled to the bone plate; and
an annular flange arranged within the through-hole, the flange having a lower surface that is co-planar with the bone-contacting surface and the locking element extends between a central opening in the annular flange;
wherein the through-hole further comprises a counter bore recess adjacent the bone-contacting surface, and
wherein the counter bore recess is arranged to substantially prevent the locking element from migrating towards the second surface of the bone plate.
21. The bone plate according to claim 20, wherein at least the first end of the locking element is welded to the counter bore recess.
22. A bone plate, comprising:
a bone-contacting surface;
a second surface opposite the bone-contacting surface, defining a plate thickness therebetween;
at least one non-threaded through-hole passing between the bone-contacting surface and the second surface;
a flange formed integrally with the through-hole, a lower surface of the flange being co-planar with the bone-contacting surface; and
a head-engaging portion that tapers from a first diameter at the second surface to a second, smaller diameter along the direction of the bone-contacting surface to engage a side portion of a head of a bone screw inserted into the through-hole, wherein the head engaging portion and the flange are configured to form a locking relationship between the bone plate and the bone screw,
wherein the head-engaging portion comprises a thin wall formed at least in part surrounding the through-hole.

23. The bone plate according to claim 22, wherein the thin wall is formed between the through-hole and one or more adjacent bores.

24. The bone plate according to claim 22, wherein the thin wall is formed between the through-hole and an annular channel surrounding the through-hole.

25. The bone plate according to claim 22, wherein the thin wall is formed between the through-hole and one or more longitudinal slits formed in the plate thickness, extending from the second surface towards the bone-contacting surface.

26. The bone plate according to claim 22, wherein the flange is positioned adjacent the bone-contacting surface.

27. The bone plate according to claim 26, wherein the head-engaging portion comprises a second flange positioned adjacent the second surface of the bone plate.

28. The bone plate according to claim 22, wherein the through-hole is configured to allow insertion of the bone screw from either the bone-contacting surface or the second surface.

29. The bone plate according to claim 22, further comprising a locking element positioned at least partially within an opening formed by the flange, the locking element being configured to engage threads of the bone screw.

30. The bone plate according to claim 22, wherein the bone plate is a low profile bone plate, having a thickness of less than about 5 mm.

31. A bone plate, comprising:
a bone-contacting surface;
a second surface opposite the bone-contacting surface, defining a plate thickness therebetween;
at least one non-threaded through-hole passing between the bone-contacting surface and the second surface, said through-hole being configured to receive a bone screw;
a locking element, wherein said locking element is configured to engage threads of the bone screw, and wherein a first end of the locking element is coupled to the bone plate; and
an annular flange arranged within the through-hole, the flange having a lower surface that is co-planar with the bone-contacting surface and the locking element extends between a central opening in the annular flange, wherein the locking element comprises a coil spring.

* * * * *